(12) United States Patent
Goldhor et al.

(10) Patent No.: US 10,473,628 B2
(45) Date of Patent: Nov. 12, 2019

(54) SIGNAL SOURCE SEPARATION PARTIALLY BASED ON NON-SENSOR INFORMATION

(71) Applicants: Speech Technology & Applied Research Corporation, Bedford, MA (US); Richard S. Goldhor, Belmont, MA (US)

(72) Inventors: Richard Goldhor, Belmont, MA (US); Keith Gilbert, Framingham, MA (US); Joel MacAuslan, Nashua, NH (US); Karen Payton, Natick, MA (US)

(73) Assignee: Speech Technology & Applied Research Corporation, Bedford, MA (US)

( * ) Notice: Subject to any disclaimer, the term of this patent is extended or adjusted under 35 U.S.C. 154(b) by 1209 days.

(21) Appl. No.: 13/933,060

(22) Filed: Jul. 1, 2013

(65) Prior Publication Data

US 2014/0195201 A1 Jul. 10, 2014

Related U.S. Application Data

(60) Provisional application No. 61/666,696, filed on Jun. 29, 2012.

(51) Int. Cl.
*G01N 29/44* (2006.01)
*G01N 29/14* (2006.01)
*G01H 3/12* (2006.01)

(52) U.S. Cl.
CPC ........... *G01N 29/4472* (2013.01); *G01H 3/12* (2013.01); *G01N 29/14* (2013.01)

(58) Field of Classification Search
CPC ............... G10L 21/028; G10L 21/0208; G10L 21/0272; G10L 19/008; H04M 9/082;
(Continued)

(56) References Cited

U.S. PATENT DOCUMENTS

2005/0213777 A1* 9/2005 Zador ............... H04R 25/40
381/94.1
2006/0034361 A1* 2/2006 Choi ............... G10L 19/008
375/224

(Continued)

OTHER PUBLICATIONS

Robert Aichner, "A real-time blind source separtaion scheme and its application to reveberant and noisy acoustic environments." (2006) 1260-1277.*

(Continued)

*Primary Examiner* — Regis J Betsch
*Assistant Examiner* — Kaleria Knox
(74) *Attorney, Agent, or Firm* — Blueshift IP, LLC; Robert Plotkin

(57) ABSTRACT

In environments (such as acoustic and bioelectrical environments) characterized by multiple simultaneous sources, effective blind source separation from sensor response mixtures becomes difficult as the number of sources increases—especially when the true number of sources is both unknown and changing over time. However, in some environments, non-sensor information can provide useful hypotheses for some sources. Embodiments of the present invention provide an adaptive filtering architecture for validating such source hypotheses, extracting an estimated representation of source signals corresponding to valid hypotheses, and improving the separation of the remaining "hidden" source signals from the sensor response mixtures.

14 Claims, 4 Drawing Sheets

The $q^{th}$ source removal from the $p^{th}$ mixture.

(58) Field of Classification Search
CPC .. A61B 5/0006; G01N 29/4472; G01N 29/14; G01H 3/12
USPC .......................... 704/205; 381/94.3, 71.6, 56
See application file for complete search history.

(56) References Cited

U.S. PATENT DOCUMENTS

| | | | | |
|---|---|---|---|---|
| 2006/0072767 | A1* | 4/2006 | Zhang | G10L 21/0208 381/71.6 |
| 2006/0176149 | A1* | 8/2006 | Douglas | A61B 5/0006 340/5.74 |
| 2009/0214052 | A1* | 8/2009 | Liu | G10L 21/0272 381/92 |
| 2010/0128897 | A1* | 5/2010 | Saruwatari | G10L 21/028 381/94.3 |
| 2010/0329472 | A1* | 12/2010 | Nakadai | H04M 9/082 381/66 |
| 2012/0322511 | A1* | 12/2012 | Fox | G10L 21/0208 455/570 |
| 2013/0294608 | A1* | 11/2013 | Yoo | G10L 21/0272 381/56 |
| 2013/0297298 | A1* | 11/2013 | Yoo | G10L 21/0272 704/205 |
| 2016/0341701 | A1 | 11/2016 | Goldhor | |
| 2017/0230654 | A1 | 8/2017 | Jung | |
| 2018/0322892 | A1 | 11/2018 | Goldhor | |

OTHER PUBLICATIONS

Robert Aichner et al., "A real-time blind source separation scheme and its application to reverberant and noisy acoustic environments," Signal Processing 86 (2006) 1260-1277.

Robert Aichner, "Acoustic Blind Source Separation in Reverberant and Noisy Environments," Doktor-Ingenieur, pp. 1-267, 2007.

Aichner, R, H Buchner, F Yan, and W Kellermann. "A Real-Time Blind Source Separation Scheme and Its Application to Reverberant and Noisy Acoustic Environments." Signal Processing 86, No. 6 (Jun. 2006): 1260-77. doi:10.1016/j.sigpro.2005.06.022.

Cover, T. M., and Joy A. Thomas, "Elements of Information Theory" Wiley Series in Telecommunications. New York: Wiley, 1991. p. 18ff.

Goldhor, Richard. "Sensor Image-Based Environmental Listening Assistant," NIH SBIR Grant No. R243 DC015416, Mar. 15, 2016.

Golub, Gene H., and Charles F. Van Loan "Matrix Computations" 3rd ed. Johns Hopkins Studies in the Mathematical Sciences. Baltimore: Johns Hopkins University Press, 1996. Chapter 5, p. 230 ff.

M. Akil and C. Serviere, "Separability of convolutive mixtures based on Wiener filtering and mutual information criterion," in Signal Processing Conference, 2006 14th European, 2006, pp. 1-4.

Matsuoka, K. "Minimal Distortion Principle for Blind Source Separation," 4:2138-43. Soc. Instrument & Control Eng. (SICE), 2002. doi:10.1109/SICE.2002.1195729.

Matsuoka, Kiyotoshi, and Satoshi Nakashima. "Minimal Distortion Principle for Blind Source Separation." In Proc. Int. Conf. Independent Component Analysis and Blind Signal Separation. Rome, 2001.

R. Aichner, H. Buchner, and W. Kellermann, "Convolutive Blind Source Separation for Noisy Mixtures," in Speech and Audio Processing in Adverse Environments, E Hänsler and G. Schmidt, Eds. Berlin, Heidelberg: Springer Berlin Heidelberg, 2008, pp. 469-524.

De Sa, A.M.F.L.M., "A note on the sampling distribution of coherence estimate for the detection of periodic signals," Signal Processing Letters, IEEE, Mar. 2004, vol. 11, No. 3, pp. 323,325.

Kay, S. M.; Modern Spectral Estimation. Englewood Cliffs, NJ: Prentice-Hall, 1988, pp. 453-455.

Ryu Takeda et al., "Speedup and Performance Improvement of ICA-based Robot Audition by Parallel and Resampling-based Blockwise Processing," The 2010 IEEE/RSJ International Conference on Intelligent Robots and Systems, Oct. 18-22, 2010, Taipei Taiwan, 8 pages.

Ryu Takeda et al., "ICA-Based Efficient Blind Dereverberation and Echo Cancellation Method for Barge-In-Able Robot Audition," ICASSP, IEEE International Conference on Acoustics, Speech and Signal Processing—Proceedings, Apr. 19-24, 2009, Taipei Taiwan, pp. 3677-3680.

* cited by examiner

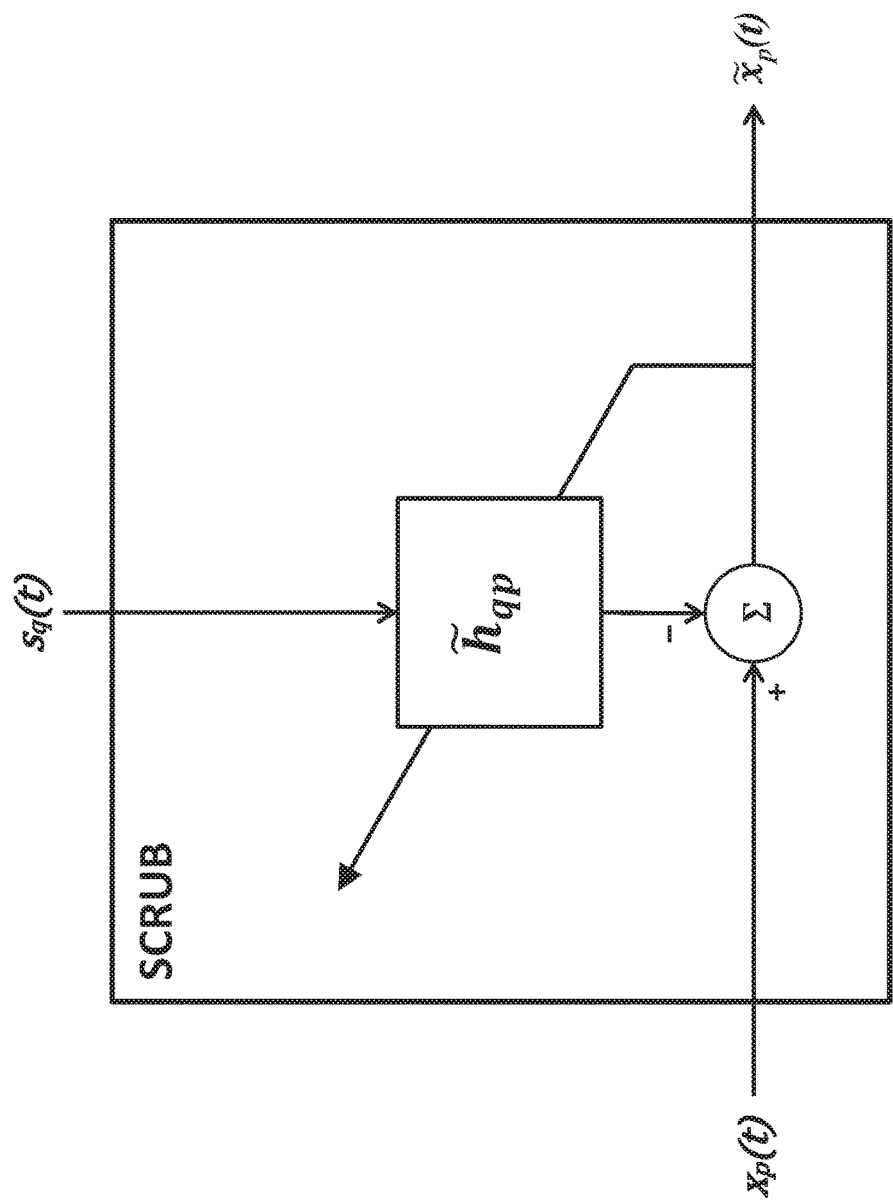
Figure 1: The $q^{th}$ source removal from the $p^{th}$ mixture.

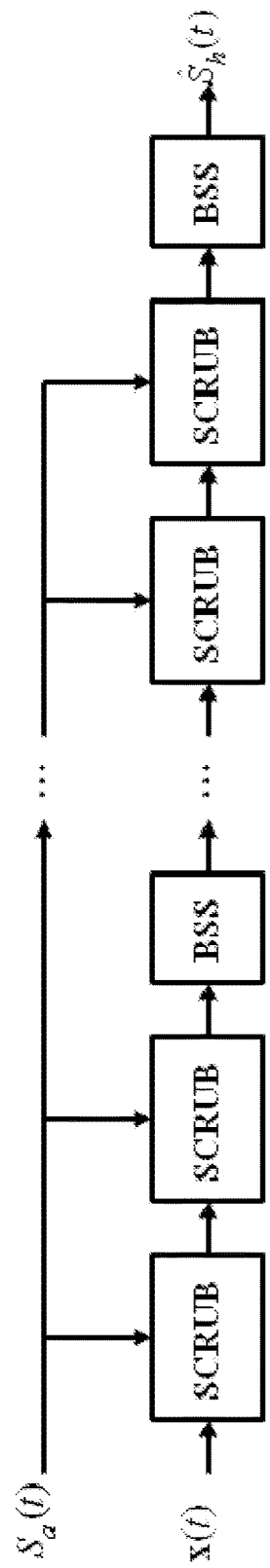
Figure 2 – Double SCRUB and BSS: semi-blind source separation enhancement.

SIGNAL SOURCE SEPARATION PARTIALLY BASED ON NON-SENSOR INFORMATION

CROSS-REFERENCE TO RELATED APPLICATIONS

This application claims priority from U.S. Provisional Patent Application Ser. No. 61/666,696, filed on Jun. 29, 2012, entitled, "Signal Source Separation," which is hereby incorporated by reference herein.

STATEMENT AS TO FEDERALLY SPONSORED RESEARCH

This invention was made with Government support under National Institutes of Health Grants R43DC006379, R43DC011668, and R43DC011475. The Government may have rights in the invention.

BACKGROUND

In many signal processing scenarios, multiple signal sources are simultaneously present, and any sensor placed in the vicinity of these sources will respond to a mixture of the active sources, rather than any single individual source. In such scenarios, the signal processing environment is the space, whether physical or virtual, in which the sources and sensors are placed, and through which signals propagate. Thus for instance, in the case of acoustic sources, the environment might be a room, and the sensors might be microphones placed in the room. The sources might be speakers (either humans or loudspeakers), telephones, etc.

For example, referring to FIG. 3A, an example is shown of a system 300 that includes a plurality of sources 302a-c and a plurality of sensors 306a-c. Although the system 300 is shown as including four sources 302a-c and three sensors 306a-c, the particular numbers of sources and sensors shown in FIG. 3A is merely an example and does not constitute a limitation of the present invention, which may be used in connection with any number of sources and any number of sensors, and any number of mixture components. The number of sources need not, in general, be equal to the number of sensors.

The sources 302a-c emit corresponding signals 304a-c. More specifically, source 302a emits signal 304a, source 302b emits signal 304b, and source 302c emits signal 304c. Although in FIG. 3A each of the sources 302a-c is shown as emitting exactly one signal, this is merely an example and does not constitute a limitation of the present invention, which may be used in connection with sources that that emit any number of signals.

In FIG. 3A, each of the sensors 306a-c receives a mixture of two or more of the signals 304a-c. In practice, any particular sensor may receive zero, one, two, or more signals. In the particular example of FIG. 3A, sensor 306a receives a mixture of signals 304a and 304b; sensor 306b receives a mixture of signals 304b and 304c; and sensor 306c receives solely signal 304b.

A signal source that contributes a mixture component with a statistically significant amount of energy to at least one sensor is called a contributing source. A source may be non-contributing either because it is inactive (not emitting a signal with any significant amount of energy) or because its location in the environment, the signal propagation properties of the environment, and/or the location of the sensors in the environment combine to shield all sensors from its contribution. Additional factors that typically determine whether a particular source is contributing or not include the spectral content of the source signal, the transfer function of the environment, and the frequency response of the sensors.

The sensors 306a-c produce corresponding outputs 308a representing their input mixtures. These outputs are also called "responses" or "response signals." For example, sensor 306a produces output 308a representing the mixture of signals 304a and 304b received by sensor 306a; sensor 306b produces output 308b representing the mixture of signals 304b and 304c received by sensor 306b; and sensor 306c produces output 308c representing the signal 304b received by sensor 306c.

Although not specifically illustrated in FIG. 3A, the contribution that a particular signal makes to the mixture received by the sensors 306a-c may vary from source to source. For example, although in FIG. 3A both sensors 306a and 306b are shown as receiving signal 304b, properties of the signal 304b may in practice differ at sensor 306a and 306b, such as due to distances in distance traveled or other factors that dampen or otherwise modify the signal 304b on its way to sensors 306a and 306b. In many systems, there is a linear relationship between a source signal and the corresponding mixture component in the response of a particular sensor. This linear relationship can be described using a so-called "transfer function" that describes the propagation characteristics between the source and the sensor.

In many cases it would be advantageous to determine, or estimate, what each of the individual source signals 304a-c is. Techniques of processing sensor signals (which are mixtures) to separate sources from each other, are referred to as "Blind Source Separation" (BSS) algorithms. Here, the word "Blind" means that the only information available to the source separation system about the sources are the sensor responses—all of which are, in general, linear weighted mixtures of multiple sources. In other words, no "hidden" information about the sources themselves is available to the source separation system. The field of BSS processing is an active field of research—see, for instance, Aichner, et al (R. Aichner, H. Buchner, F. Yan, and W. Kellerman, "A real-time blind source separation scheme and its application to reverberant and noisy acoustic environments", Signal Processing, vol. 86, pp. 1260-1277, 2007) for a detailed description of a BSS algorithm.

As applied to FIG. 3A, for example, BSS may be used in an attempt to process the outputs 308a-c of sensors 306a-c, respectively, to identify the source signals 304a-c. For example, the system 300 of FIG. 3A includes a blind source separation module 310 which receives the signals 308a-c output by the sensors 306a-c and generates, based solely on those sensor outputs 308a-c, source identification outputs 312a-c which are intended to identify the source signals 304a-c that caused the sensors 306a-c to produce the outputs 308a-c. For example, the blind source separation module 310 may be used to process outputs 308a, 308b, and 308c (e.g., simultaneously) to produce outputs 312a-c, where output 312a is intended to estimate source signal 304a; output 312b is intended to estimate source signal 304b; and output 312c is intended to estimate source signal 304c.

SUMMARY

In environments (such as acoustic and bioelectrical environments) characterized by multiple simultaneous sources, effective blind source separation from sensor response mixtures becomes difficult as the number of sources increases—especially when the true number of sources is both unknown and changing over time. However, in some environments, non-sensor information can provide useful hypotheses for some sources. Embodiments of the present invention provide an adaptive filtering architecture for validating such source hypotheses, extracting an estimated representation of source signals corresponding to valid hypotheses, and improving the separation of the remaining "hidden" source signals from the sensor response mixtures.

BRIEF DESCRIPTION OF THE DRAWINGS

FIG. 1 shows an adaptive filtering representation of removing a source from a mixture of sources according to one embodiment of the present invention;

FIG. 2 is a diagram illustrating a process involving performing a SCRUB operation twice and then performing a BSS operation, and then repeating the process indefinitely according to one embodiment of the present invention;

DETAILED DESCRIPTION

Figure 3A:
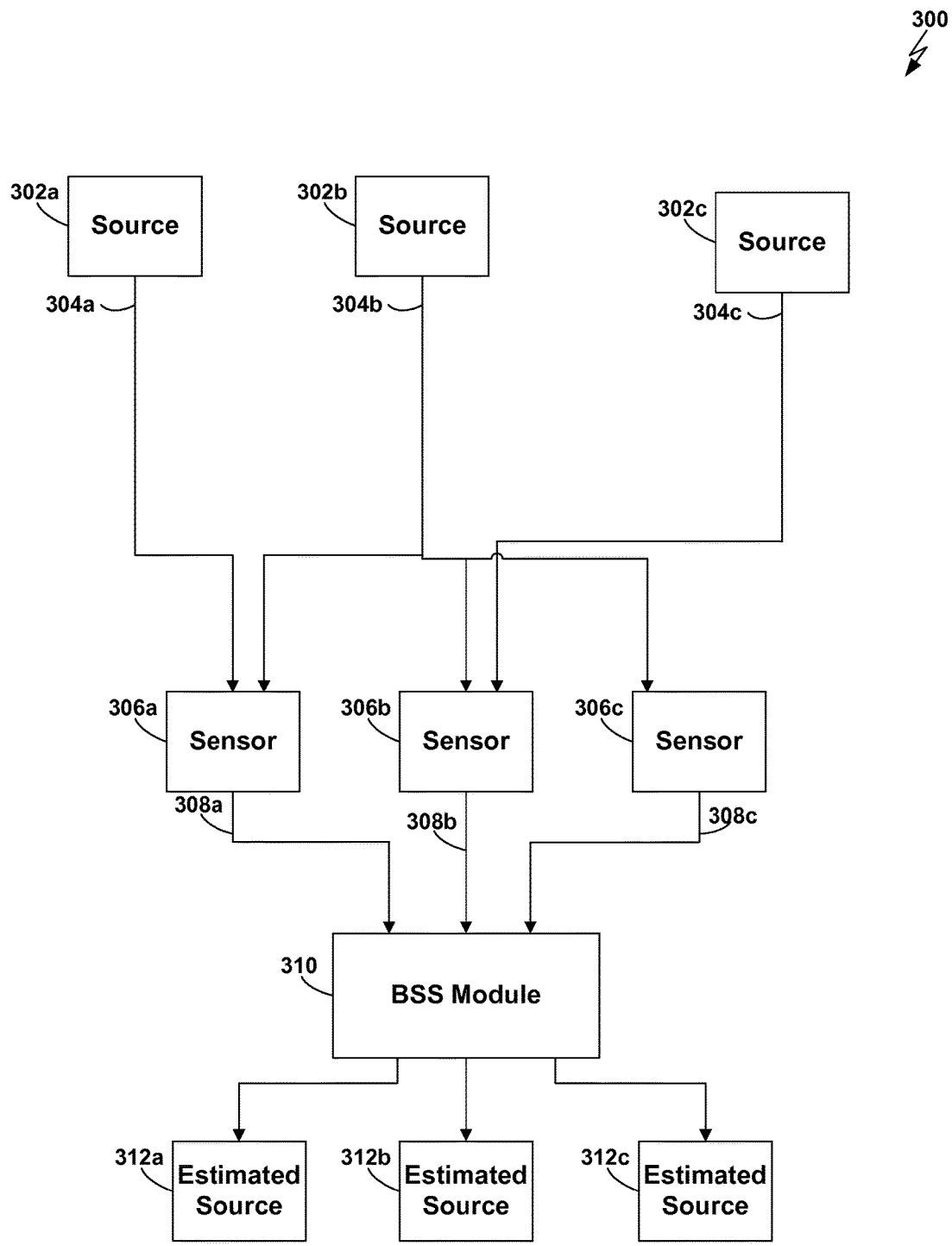
FIG. 3A is a diagram illustrating a prior art Blind Source Separation (BSS) system.
Figure 3B:
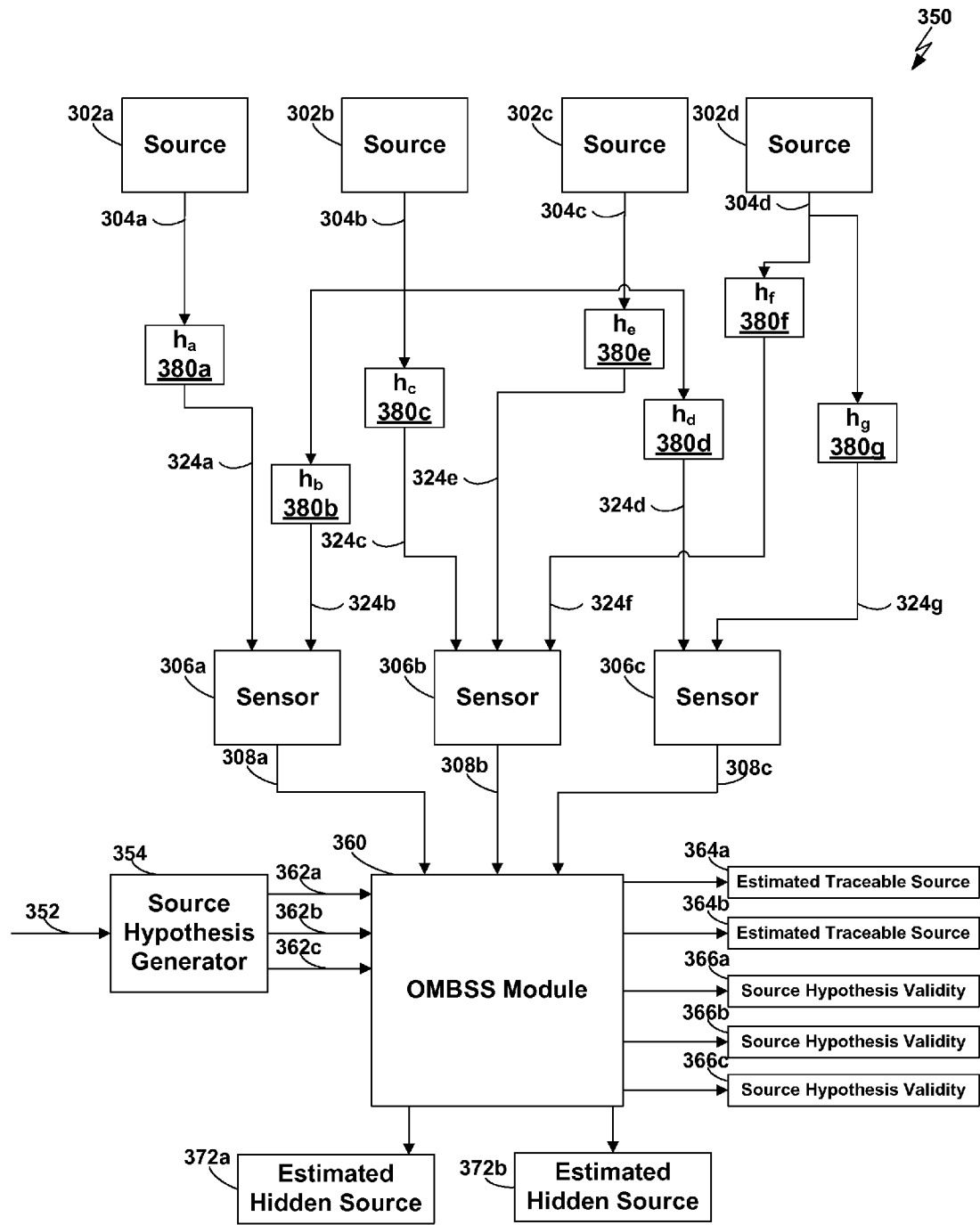
FIG. 3B is a diagram illustrating a Blind Source Separation (BSS) system according to one embodiment of the present invention.

Embodiments of the present invention involve a modification to Blind Source Separation that is referred to herein as Only Mostly Blind Source Separation (OMBSS). For example, referring to FIG. 3B, an OMBSS system 350 implemented according to one embodiment of the present invention is shown. The OMBSS system 350 includes the sources 302a-c and signals 304a-c, but also includes an additional source 302d, which emits signal 304d. As in the system 300 of FIG. 3A, in the system 350 of FIG. 3B the sensor 306a receives a mixture of signals 304a and 304b. In the system 350 of FIG. 3B, the sensor 306b receives a mixture of signals 304b, 304c, and 304d; and sensor 306c receives a mixture of signals 304b and 304d. The OMBSS system 350 of FIG. 3B, like the BSS system 300 of FIG. 3A, includes sensors 306a-c. As the example in FIG. 3B illustrates, the number of sources 302a-d may be greater than the number of sensors 306a-c in embodiments of the present invention.

The OMBSS system 350 explicitly models the environmental transfer functions as filters 380a-g, each of which receives one of the source signals 304a-d as an input and produces a filtered source signal as an output. (Although the BSS system 300 of FIG. 3A also explicitly models the environmental transfer functions as filters, such filters are omitted from FIG. 3A for ease of illustration.) In particular, for each source A that contributes a source signal received by a sensor B, a corresponding transfer function filter $h_{A,B}$ filters the signal from source A to produce the potentially delayed and filtered signal that is received by sensor B. Any two or more such filters may differ from each other (i.e., they may apply different filtering functions to their inputs). In particular, in the example of FIG. 3B:

Filter 380a filters source signal 304a to produce filtered source signal 324a, which is received as an input by sensor 306a.

Filter 380b filters source signal 304b to produce filtered source signal 324b, which is received as an input by sensor 306a.

Filter 380c filters source signal 304b to produce filtered source signal 324c, which is received as an input by sensor 306b.

Filter 380d filters source signal 304b to produce filtered source signal 324d, which is received as an input by sensor 306c.

Filter 380e filters source signal 304c to produce filtered source signal 324e, which is received as an input by sensor 306b.

Filter 380f filters source signal 304d to produce filtered source signal 324f, which is received as an input by sensor 306b.

Filter 380g filters source signal 304d to produce filtered source signal 324g, which is received as an input by sensor 306c.

Therefore, any reference herein to one of the sensors 306a-c receiving one of the signals 304a-d should be understood to refer to that sensor receiving a filtered version of the specified signal. For example, any reference herein to sensor 306a receiving signal 304a should be understood to refer to sensor 306a receiving filtered signal 324a, which is a filtered signal resulting from using filter 380a to filter signal 304a. As the example of FIG. 3B illustrates, any two sensors which receive the "same" one of the signals 304a-d in fact receive different filtered versions of that signal. For example, although it may be said that both sensors 306a and 306b receive signal 304b, in fact sensor 306a receives filtered signal 380b and sensor 306b receives filtered signal 380c, both of which are filtered versions of the same signal 304b. Similarly, any reference herein to a "mixture of signals" received from two or more sources should be understood to refer to a mixture of filtered signals received from such sources. For example, any reference herein to sensor 306a receiving a mixture of signals 304a and 304b should be understood to refer to sensor 306a receiving a mixture of filtered source signals 324a and 324b.

The OMBSS system 350 includes an OMBSS module 360 that performs the functions performed by the BSS module 310 of FIG. 3A, along with additional functions described below. In general, OMBSS leverages the fact that sometimes there is in fact additional information available to a source separation system (such as system 350) about the sources (such as sources 302a-c). For example, one or more signals might be available to the OMBSS module 360, each of which is similar to a single one of the sources 302a-c. We call such a signal a source hypothesis signal. In general, a source hypothesis signal is hypothesized to be coherent with one of the sources 302a-c. In particular, each source hypothesis signal is hypothesized to have unit coherence with exactly one of the sources 302a-c, and zero coherence with all other sources.

The value of the coherence function between two signals ranges between 1.0 and 0.0, inclusive. de Sa, A. M. F. L. M., "A note on the sampling distribution of coherence estimate for the detection of periodic signals," *Signal Processing Letters, IEEE*, vol. 11, no. 3, pp. 323, 325, March 2004. In theory, two signals that are mutually incoherent will have a coherence function value of zero, while two signals that are perfectly coherent will have a coherence function value of one. In practice, because of the presence of noise (in the system instruments, electronics, computers, etc.) the actual coherence values may vary somewhat. Appropriate statistical tests can be used to determine whether a calculated coherence value differs significantly from zero or one, and whether two calculated coherence values differ significantly from each other. We will use the term "incoherent" to describe two signals whose coherence value does not differ significantly from zero, and may also describe such signals as having "zero coherence." We will use the phrases "perfectly coherent" or "having unit coherence" to describe two signals whose coherence value does not differ significantly from one. Except where indicated otherwise, the term "coherent" applied to two signals means that those signals have a coherence function value significantly greater than zero. Except where clearly indicated otherwise, the term "significant" means "statistically significant."

A source hypothesis is said to be "associated with" the source with which it is hypothesized to be coherent. For example, in FIG. 3B, a source hypothesis signal 362a, which is associated with source 302a, is available as an input to the OMBSS module 360. Similarly, a source hypothesis signal 362b, which is associated with source 302b, is available as an input to the OMBSS module 360. Furthermore, a source hypothesis signal 362c, which is not associated with any of the sources 302a-c in the system 350, is available to the OMBSS module 360. Solely for purposes of example, no source hypothesis signal associated with source 302c or 302d is available to the OMBSS module 360. The particular set of source hypotheses available to the OMBSS module 360 in FIG. 3B is merely an example and does not constitute a limitation of the present invention.

Alternatively, the available additional information about a source might be descriptive information other than a signal that is coherent with the source signal itself. For example, if the source signal were a pure tone, the descriptive information associated with that source might be the frequency of the pure tone. Or, if the source signal were a musical composition, the associated descriptive information might be the name of the composition, or the musical score for the composition. We call such information about a source a source hypothesis description.

In the OMBSS model, a source hypothesis signal can be generated from a source hypothesis description via an appropriate source hypothesis generator. For example, the OMBSS system 350 of FIG. 3B may include a source hypothesis generator 354, which may receive a source hypothesis description 352 as an input, and generate, based on the source hypothesis description 352, the source hypothesis signals 362a-c. There are many different types of source hypothesis generators, which are, in general, matched with the characteristics of the source hypothesis descriptions they can process to generate a source hypothesis signal. For example, a tone generator is a source hypothesis generator that accepts a frequency value as an input source hypothesis description, and outputs a pure tone with the specified frequency as a source hypothesis signal. A speech synthesizer is a source hypothesis generator that accepts as input a source hypothesis description comprising an orthographic or phonetic description of speech, and which generates as output a source hypothesis signal that takes the form of a corresponding speech signal.

The source hypothesis generator 354, however, is not a required component of the system 350. The source hypothesis generator 354 may, for example, be omitted from the system 350, in which case the source hypothesis signals 362a-c may be available for use despite not having been generated from any identifiable source hypothesis generator from an explicit source hypothesis description. As a result, the OMBSS module 360 may receive one or more of the source hypothesis signals 362a-c from some source other than the source hypothesis generator 354. For example, the source hypothesis generator 354 may be included in the system 350, but need not be the source of all source hypothesis signals received by the OMBSS module 360. For example, the OMBSS module 360 may receive as inputs a plurality of source hypothesis signals, some of which were generated by the source hypothesis generator 354, and some of which were not generated by any source hypothesis generator. In general, all, some, or none of the source hypothesis signals received as inputs by the OMBSS module 360 may be generated by the source hypothesis generator 354. Similarly, all, some, or none of the source hypothesis signals received by the OMBSS module 360 may not be generated by any source hypothesis generator.

A source hypothesis description may itself comprise a signal. For instance, if a source is hypothesized to be a poor quality loudspeaker playing music broadcast by an FM classical music station, an associated source hypothesis description might comprise a high-quality version of the FM broadcast signal, accompanied by a linear filter model of the loudspeaker. In this case, an appropriate source hypothesis generator would be a linear filter (perhaps implemented in software) that could model the loudspeaker and be used to filter the FM broadcast signal to generate an appropriately low-fidelity output signal. This output signal would be the source hypothesis signal for the loudspeaker.

Furthermore, although only a single source hypothesis signal 362a is shown for source 302a, this is merely an example and does not constitute a limitation of the present invention. From time to time, multiple source hypotheses may be available to the OMBSS module 360 for any particular source, and source hypotheses may be available for a signal source, multiple sources, all sources, or none of the sources. Furthermore, a single source hypothesis description may generate more than one source hypothesis signal, which may be alternative hypotheses for a single source, or simultaneous hypotheses for multiple sources.

A single source hypothesis signal may usefully be compared with a sensor response signal: unlike a sensor response signal, a source hypothesis signal is "pure," in that it is, by hypothesis, coherent with only one source. A source hypothesis signal never represents a mixture of source signals. For example, the OMBSS module 360 may compare the source hypothesis signal 362a to one or more of the sensor outputs 308a, 308b, and 308c individually. Similarly, the OMBSS module 360 may compare the source hypothesis signal 362b to one or more of the sensor outputs 308a, 308b, and 308c individually.

Unlike a sensor response signal, a source hypothesis signal is not necessarily valid. The source with which it is associated may not actually be active in the environment, or might not be a contributing source. As a result, the source with which the source hypothesis signal is associated may not actually be contributing to any sensor response in the system 350. For example, in the system 350 of FIG. 3B, source hypothesis signal 362c is associated with a hypothetical source that does not, in fact, contribute any energy to any of the sensor responses in the system 350. As a result, the source with which source hypothesis signal 362c is associated does not produce a signal that is received by any of the sensors 306a-c in the system, and therefore does not contribute to any of the sensor outputs 308a-c.

A valid source hypothesis signal is a source hypothesis signal that is in fact significantly coherent with at least one of the sensor responses in the system 350. An invalid source hypothesis signal is a source hypothesis signal whose coherence with all of the sensor responses in the system 350 is insignificantly different from zero. By extension, source hypotheses and source hypothesis descriptions are valid (invalid) when their corresponding source hypothesis signals are valid (invalid).

In summary, source hypotheses (e.g., source hypotheses 362a-c) are pure, but possibly invalid, and even when they are valid, in practice source hypotheses are only significantly coherent with their associated source—they are, in general, not equal either to the source signal itself, or the source's mixture component in any sensor response. Sensor responses (e.g., sensor responses 308a-c), on the other hand, are always valid, but are generally impure—they are mixtures of components contributed by multiple incoherent sources.

Embodiments of the present invention use source hypotheses (e.g., source hypotheses 362a-c) to improve source separation. As a result, in practice embodiments of the present invention may produce better results (i.e., better estimated sources 372a-b) than BSS. Put another way, in cases where information associated with source signals are available, that information can be used in conjunction with BSS processing to generate a better estimate of the hidden sources than is available from sensor mixtures alone. Here, "better" generally means source estimations that are of higher fidelity and are more completely separated from other sources.

Another advantage of OMBSS processing is that it may reduce the number of components in one or more response mixtures, which typically improves the quality of the final result and/or reduces the amount of input data and processing time required to converge on a final estimate. Yet another advantage of OMBSS processing is that it may eliminate one or more hidden sources completely—that is, convert them from "hidden" to "known". Often, if the number of hidden sources in a particular signal scenario can be reduced, the amount of input data and processing time required for the BSS algorithm to converge on an estimate of the remaining sources is reduced, and the quality of the resulting estimates improved. Indeed, although there exist BSS algorithms that can separate more underlying sources than there are sensor response signals to process, many attractive BSS algorithms assume that the number of underlying hidden source signals is equal to, or at least no greater than, the number of sensor response signals. In practice, using OMBSS processing to "scrub" excess source components from a set of sensor response signals may represent the difference between effective separation of the remaining hidden sources, and the inability to effectively separate the mixtures, due to violation of the BSS algorithm's underlying assumptions and requirements.

A related advantage of OMBSS processing is that in some circumstances, all of the components in one or more sensor outputs may be associated with source hypothesis signals, so that those sensor outputs do not have to be submitted for BSS processing at all, thereby reducing the complexity of the required BSS processing, reducing convergence time, and/or improving the quality of the final BSS estimates. A set of sensor outputs whose number has been reduced by eliminating one or more outputs, all of whose mixture components have been identified as traceable, is referred to as a reduced, or deflated, response set.

A traceable source is any source associated with a valid source hypothesis. In the example of FIG. 3B, OMBSS module 360 outputs estimated traceable source signals 364a and 364b, which are associated with valid ones of the source hypothesis signals 362a-c. Once a source has been determined to be traceable, it is no longer completely blind—hence the sobriquet "Only Mostly Blind Source Separation". Each valid hypothesis is significantly coherent with a response component of at least one response signal. We call such a component a traceable response component, or simply a traceable component. Each traceable component is associated with exactly one valid source hypothesis signal. An invalid source hypothesis has no traceable components associated with it.

Since each traceable component associated with a given valid hypothesis is coherent with the corresponding hypothesis signal, that set of traceable components may be used to estimate the underlying traceable source. Such an estimate is called a traceable source estimate.

A number of alternative techniques are available for estimating the traceable source signal from the source hypothesis signal and the traceable components. Possibilities include, but are not limited to, the following:

A. Using the source hypothesis signal as the traceable source estimate.

B. Selecting one of the traceable source components as the traceable source estimate. Possible selection criteria include selecting the component with the most power, selecting the component with the widest range of frequencies, and selecting the component that is most coherent with the source hypothesis signal.

C. Forming the traceable source signal as a complex weighted sum of all of the traceable components of the given source hypothesis, where by "complex weighted sum" is meant forming a mixture of the traceable components, each convolved with a complex "kernel" vector calculated to maximize or minimize an application-appropriate metric, such as the mutual correlation of the weighted terms.

D. Forming the traceable source signal using any of the techniques above, and further delaying or advancing the signal in a useful way. For example, adjusting the delay of the estimated traceable source signal so that the relative delay of one of the traceable source components is set to a desired value, for example zero. This corresponds to modeling the position in space of the traceable source to be identical to the position of the sensor whose traceable component has a zero delay.

It should be noted that two source hypothesis signals may be mutually coherent. For instance, this situation may arise when a particular source hypothesis description is ambiguous, and the associated source hypothesis generator generates two or more alternative, partially coherent, hypothesis signals from a single description. Alternatively, two source hypothesis signals, arising independently either from two source hypothesis generators or from other origins, may happen to be coherent. In the alternative, it may be possible to determine from the details of the origins of source hypothesis signals that all simultaneous source hypotheses are mutually incoherent.

The possibility of mutually coherent source hypothesis signals gives rise to the possibility of generating mutually coherent traceable source estimates. In such cases, the user of the traceable source estimates may need to decide, based on application-specific criteria, which source hypothesis is superior.

The other issue that arises when mutually coherent source hypotheses may be present is the way in which valid hypothesis signals are to be scrubbed from each sensor response signal. As discussed below, in general such scrubbing may be performed either sequentially or jointly. In the presence of potentially coherent source hypotheses, the use of a sequential scrubbing architecture suffers from the disadvantage that the order of scrubbing will, in general, affect the coherence of the identified traceable components. Joint scrubbing architectures, or parallel scrubbing architectures, do not suffer from this disadvantage, because they do not impose any sequence on the order in which hypothesis signals are scrubbed.

As shown in FIG. 3B, OMBSS module element 360 has three types of outputs. First, the module 360 generates source hypothesis validity codes 366a-c, one for each of its input source hypothesis signals 362a-c. At any given time, each validity code output assumes one of the following three possible values:

Hypothesis validity unknown: the validity of the corresponding source hypothesis is currently unknown;

Hypothesis valid: the corresponding source hypothesis has been determined to be currently valid;

Hypothesis invalid: the corresponding source hypothesis has been determined to be currently invalid.

Second, the OMBSS module generates a traceable source signal estimate corresponding to each detected traceable source signal. Finally, the OMBSS module generates a hidden source signal estimate for each detected hidden source. The number of validity code outputs equals the number of source hypothesis signal inputs. The number of traceable signal outputs equals the number of detected traceable source signals, and the number of hidden signal outputs equals the number of detected hidden sources.

One particular context in which embodiments of the present invention are often useful is the processing of acoustic signals. In the acoustic case, the "hidden" sources are acoustic sources (e.g., noise sources, talkers, loudspeakers, etc.), the sensors are microphones, and an important class of source hypotheses is the class of "pre-acoustic" signals, such as the audio signals that feed loudspeakers. For example, in an airport gate area, there are many simultaneously-active acoustic sources. A microphone anywhere in the gate area will pick up a mixture of many sources. One of those sources might frequently be a CNN broadcast, with the audio coming from loudspeakers mounted in the ceiling. The acoustic radiation from one such speaker is an acoustic source. A relevant source hypothesis description or signal is the audio channel of the CNN broadcast. The electronically broadcast audio signal is not precisely the acoustic output of the speaker itself (it doesn't, for instance, reflect the loudspeaker's frequency characteristics), but it is strongly coherent with the loudspeaker's acoustic output.

We now present in greater technical detail one basic method of employing source hypothesis signals to improve BSS, and then a multi-stage enhancement to the basic method. In this exposition we treat OMBSS as an enhancement to the blind source separation problem that employs a priori known source signals (the source hypotheses). Although the principles proposed here apply to the broader settings of general estimation within nonlinear and post-nonlinear mixing scenarios, we use adaptive filtering within a linear (convolutive) mixing network as an example. Given a set of L-length source vectors $S=\{s_q(t)\}_{q=1}^Q$ at time t where the $q^{th}$ source vector is $s_q(t)=[s_q(t),s_q(t-1), \ldots, s_q(t-L+1)]^T$ and $s_q(t)$ is an individual source sample, the set of convolutive mixtures, $\{x_p(t)\}_{p=1}^P$ is given by, $$x_p(t) = \sum_{q=1}^{Q} h_{qp}^T(t)s_q(t), \ p=1, \ldots, P$$

where $h_{qp}^T(t)$ is an L-length vector of filter coefficients. Although $h_{qp}^T(t)$ is possibly time-varying, we now drop the time-dependence for clarity of presentation and assume that the individual filters, $h_{qp}$ for $q=1, \ldots, Q$ and $p=1, \ldots, P$, are static. The goal of the source separation problem is to recover S up to some arbitrary constant filtering and permutation (if S is considered as an ordered set).

Now consider the case where R sources are known a priori, such that the source set can be divided into two complementary subsets $S_a(t)=\{s_q(t)\}_{q=1}^R$ and $S_h(t)=\{s_q(t)\}_{q=R+1}^Q$. We are making the assumption that all sources in S are actually present in the mixtures, and we do not address the problem of detecting the known source set, $S_a(t)$, in the mixtures. For each of the R known sources we wish to estimate the forward mixing filters $h_{qp}$ for $q=1, \ldots, R$ and $p=1, \ldots, P$, and then use those estimates to remove, or SCRUB, the filtered estimates of $S_a(t)$ from the mixtures. FIG. 1 shows an adaptive filtering representation of removing the $q^{th}$ source from the $p^{th}$ mixture.

Thus, speaking informally about the process shown in FIG. 1, we say that the adaptive filter shown in FIG. 1 "scrubs" the $q^{th}$ source hypothesis signal from the $p^{th}$ sensor response mixture.

For the $p^{th}$ mixture, the source removal can be performed by jointly estimating $\{\hat{h}_{qp}\}_{q=1}^R$ or estimating the individual $\hat{h}_{qp}$ for $q=1, \ldots, R$ sequentially in a deflationary manner. In either case, the filter estimation will take place in the presence of multiple interfering sources, resulting in a filter mismatch $\tilde{h}_{qp}=h_{qp}-\hat{h}_{qp}\neq 0$ which leaves a residual of the set $S_a(t)$ remaining in the mixture. However, since the power of the individual sources in $S_a(t)$ have been reduced in the mixture leaving the hidden sources $S_h(t)$ as the predominant source power, performing the source removal a second time to estimate the known sources', $S_a(t)$'s, residuals will be more effective since the estimation will take place, effectively, in the presence of Q–R interferers as opposed to the original Q–1 interferers. Denoting $h'_{qp}$ as the residual filter of the $q^{th}$ source the $p^{th}$ mixture, then there will be a filter mismatch $\tilde{h}'_{qp}=h'_{qp}-\hat{h}'_{qp}\neq 0$ thus leaving a residual.

We denote the $p^{th}$ deflated mixture of this "double SCRUB" method just outlined as, $$x'_p(t) = x_p(t) - \sum_{q=1}^{R} \hat{h}_{pq}^T s_q(t) - \sum_{q=1}^{R} \hat{h}'^T_{pq} s_q(t)$$

The set of deflated mixtures $X'=\{x'_p(t)\}_{p=1}^P$ can be input into a blind source separation (BSS) algorithm where $x'_p(t)=[x'_p(t),x'_p(t), \ldots, x'_p(t-M+1)]^T$ and M is some number of algorithm-dependent samples. Assuming that the BSS method is able to (at least, partially) separate the hidden sources such that the BSS outputs are estimates of the hidden sources, $\hat{S}_h(t)$, then the double SCRUB method can be repeated on the BSS outputs, since the residual estimates will now be carried out under an even further reduced interference set. Indeed, the individual known source residuals will be estimated in the presence of one predominant interfering source and Q–2 (presumably low-power) residuals. The output of the double SCRUB can then be fed into the BSS algorithm again, since the resulting reduction in residual power will allow a better source separation estimate. Denoting the vector of mixture observations at time t as $x(t)=[x_1(t),x_2(t), \ldots, x_p(t)]^T$, this process of double SCRUB then BSS can then be performed indefinitely to enhance the BSS solution, as is shown in FIG. 2.

In general, when a source hypothesis signal has been scrubbed from all of the sensor response signals, the associated traceable source has been removed as a possible hidden source that makes any contribution to the scrubbed response signals. That is, the scrubbed responses signals are all incoherent with the given source hypothesis signal.

Similarly, whenever the power in a scrubbed sensor response signal is zero, or not significantly greater than zero, and it has any traceable components, then that sensor response mixture can be considered to consist solely of traceable components, all of which have been scrubbed, and none of which correspond to hidden sources. In this case, the response signal does not need to be processed by the BSS algorithm, and eliminating it as an input (i.e., reducing the response set) may have computational and performance advantages.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

For example, although the acoustic situation is an important one, embodiments of the present invention are not limited to use in conjunction with acoustic signals, but rather may be used additionally or alternatively with other kinds of signals. For example, embodiments of the present invention may be used in conjunction with bioelectrical signals (e.g., bioelectrical signals in the human body), in which case the sensors may be electrodes and the sources may be neural signals.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

What is claimed is:

1. A method for modifying at least one input signal to a source separation module, the method performed by at least one computer processor executing computer program instructions stored on at least one non-transitory computer-readable medium, the method for use in a signal processing environment comprising a space in which a plurality of contributing signal sources and at least one sensor are placed and in which the signal contributed by a source propagates to the at least one sensor, which responds to a mixture of the propagated signals, the method comprising:
    (A) receiving, from a sensor in the signal processing environment, a sensor response signal that includes a mixture of a plurality of response components, each of the plurality of response components being a delayed and filtered version of a corresponding signal emitted by one of the plurality of contributing sources;
    (B) receiving a source hypothesis signal, not generated by any sensor in the signal processing environment, that is coherent with exactly one of the plurality of contributing sources;
    (C) estimating a filter that, when applied to the received source hypothesis signal, generates an estimated response component of the sensor response signal;
    (D) generating the estimated response component by applying the filter to the received source hypothesis signal;
    (E) scrubbing the sensor response signal by subtracting the estimated response component from the sensor response signal to produce a scrubbed response signal that is incoherent with the source hypothesis signal; and
    (F) providing the scrubbed response signal to the source separation module.

2. The method of claim 1, wherein the source hypothesis signal is provided as an input to a first one of at least one source, and wherein the first one of the at least one source generates a first source output signal that differs from and is coherent with the source hypothesis signal.

3. The method of claim 1, wherein the source hypothesis signal is generated by a source hypothesis generator from a source hypothesis description.

4. A non-transitory computer-readable medium having computer program instructions stored thereon, wherein the computer program instructions are executable by a computer processor to perform a method for modifying at least one input signal to a source separation module, the method for use in a signal processing environment comprising a space in which a plurality of contributing signal sources and at least one sensor are placed and in which the signal contributed by a source propagates to the at least one sensor, which responds to a mixture of the propagated signals, the method comprising:
  (A) receiving, from a sensor in the signal processing environment, a sensor response signal that includes a mixture of a plurality of response components, each of the plurality of response components being a delayed and filtered version of a corresponding signal emitted by one of the plurality of contributing sources;
  (B) receiving a source hypothesis signal, not generated by any sensor in the signal processing environment, that is coherent with exactly one of the plurality of contributing sources;
  (C) estimating a filter that, when applied to the received source hypothesis signal, generates an estimated response component of the sensor response signal;
  (D) generating the estimated response component by applying the filter to the received source hypothesis signal;
  (E) scrubbing the sensor response signal by subtracting the estimated response component from the sensor response signal to produce a scrubbed response signal that is incoherent with the source hypothesis signal; and
  (F) providing the scrubbed response signal to the source separation module.

5. The non-transitory computer-readable medium of claim 4, wherein the source hypothesis signal is provided as an input to a first one of at least one source, and wherein the first one of the at least one source generates a first source output signal that differs from and is coherent with the source hypothesis signal.

6. The non-transitory computer-readable medium of claim 4, wherein the source hypothesis signal is generated by a source hypothesis generator from a source hypothesis description.

7. The method of claim 1, wherein the one of the plurality of contributing sources comprises an acoustic source, and wherein the at least one sensor comprises an acoustic sensor.

8. The non-transitory computer-readable medium of claim 4, wherein the one of the plurality of contributing sources comprises an acoustic source, and wherein the at least one sensor comprises an acoustic sensor.

9. The method of claim 1, wherein the one of the plurality of contributing sources comprises a bioelectrical source, and wherein the at least one sensor comprises a bioelectrical sensor.

10. The non-transitory computer-readable medium of claim 4, wherein the one of the plurality of contributing sources comprises a bioelectrical source, and wherein the at least one sensor comprises a bioelectrical sensor.

11. The method of claim 1, wherein estimating the filter comprises using adaptive filtering to estimate the filter.

12. The non-transitory computer-readable medium of claim 4, wherein estimating the filter comprises using adaptive filtering to estimate the filter.

13. The method of claim 1, wherein the filter comprises a forward mixing filter, and wherein scrubbing the estimated response component from the sensor response signal comprises using the forward mixing filter to scrub the estimated response component from the sensor response signal.

14. The non-transitory computer-readable medium of claim 4, wherein the filter comprises a forward mixing filter, and wherein scrubbing the estimated response component from the sensor response signal comprises using the forward mixing filter to scrub the estimated response component from the sensor response signal.

* * * * *